(12) United States Patent
Stevens et al.

(10) Patent No.: US 11,700,904 B2
(45) Date of Patent: Jul. 18, 2023

(54) WIRELESS CHARGING ASSEMBLIES FOR SENSORIZED INSOLES, METHODS FOR CHARGING SENSORIZED INSOLES, AND FOOTWEAR SYSTEMS INCLUDING SENSORIZED INSOLES

(71) Applicant: ORPYX MEDICAL TECHNOLOGIES INC., Calgary (CA)

(72) Inventors: Travis Stevens, Calgary (CA); Michael Purdy, Calgary (CA); Kogan Lee, Calgary (CA); Paul Garrity, Rockwall, TX (US)

(73) Assignee: ORPYX MEDICAL TECHNOLOGIES INC., Calgary (CA)

( * ) Notice: Subject to any disclaimer, the term of this patent is extended or adjusted under 35 U.S.C. 154(b) by 0 days.

(21) Appl. No.: 17/525,092

(22) Filed: Nov. 12, 2021

(65) Prior Publication Data
US 2023/0148701 A1  May 18, 2023

(51) Int. Cl.
*A43B 3/34* (2022.01)
*H02J 50/00* (2016.01)
(Continued)

(52) U.S. Cl.
CPC .............. *A43B 3/34* (2022.01); *A61B 5/1038* (2013.01); *A61B 5/6807* (2013.01);
(Continued)

(58) Field of Classification Search
CPC ..... A43B 1/0054; A43B 3/0005; A43B 3/001; A43C 1/00; A43C 11/008; A43C 11/165; H02J 50/10; H02J 7/0042; H02J 7/025
See application file for complete search history.

(56) References Cited

U.S. PATENT DOCUMENTS 8,058,837 B2   11/2011   Beers et al.
10,004,428 B2   6/2018   Everett et al.
(Continued)

FOREIGN PATENT DOCUMENTS

WO   2021092676 A1   5/2021

OTHER PUBLICATIONS

Semtech Wireless Charging User Guide TSWIRX-5V2-EVM Low Power Wireless Charging Receiver (Rev 3.00).
(Continued)

*Primary Examiner* — Quan Tra
(74) *Attorney, Agent, or Firm* — ABM Intellectual Property Inc.; Adrienne Bieber McNeil (57) ABSTRACT

A footwear system includes a sensorized insole and a charger. The sensorized insole has an insole bulk having a foot-facing upper surface. A sensor is embedded in the insole bulk for measuring a parameter of a user's foot, a battery is embedded in the insole bulk for providing energy to the sensor, and a receiver pod is embedded in the insole bulk and is spaced from the foot-facing upper surface for wirelessly receiving energy and providing energy to the battery. The charger provides energy to the receiver pod, and includes a cable for connecting to an energy source, and a transmitter pod electrically connected to the cable for receiving energy from the cable and wirelessly transmitting energy to the receiver pod. The transmitter pod is positionable against the foot-facing upper surface to wirelessly provide energy to the receiver pod through the insole bulk.

16 Claims, 5 Drawing Sheets

(51) Int. Cl.
 *A61B 5/00* (2006.01)
 *A61B 5/103* (2006.01)
 *H01R 13/62* (2006.01)
 H02J 50/10 (2016.01)
 H02J 50/05 (2016.01)

(52) U.S. Cl.
 CPC ....... *A61B 5/6829* (2013.01); *H01R 13/6205* (2013.01); *H02J 50/005* (2020.01); *H02J 50/05* (2016.02); *H02J 50/10* (2016.02)

(56) References Cited

U.S. PATENT DOCUMENTS

| | | | | |
|---|---|---|---|---|
| 2012/0186101 A1* | 7/2012 | Sanchez | ................. | A43B 11/00 36/43 |
| 2014/0197693 A1* | 7/2014 | Fujita | ..................... | H02J 50/60 307/104 |
| 2014/0354218 A1 | 12/2014 | Kaynar et al. | | |
| 2015/0326028 A1* | 11/2015 | Suzuki | ................ | H02J 7/00034 307/104 |
| 2016/0101291 A1 | 4/2016 | Jaax et al. | | |
| 2016/0156388 A1* | 6/2016 | Zeine | ................... | H04W 76/14 307/104 |
| 2016/0181870 A1* | 6/2016 | Bae | ......................... | H02J 50/12 307/104 |
| 2017/0150773 A1* | 6/2017 | Beers | ................... | A43C 11/165 |
| 2017/0201130 A1* | 7/2017 | Park | ................... | H02J 7/00045 |
| 2018/0034305 A1* | 2/2018 | Lee | ........................ | H02J 50/10 |
| 2020/0021896 A1* | 1/2020 | Fitzgerald | ............. | A61B 5/002 |
| 2020/0060378 A1* | 2/2020 | Roh | ......................... | A43B 3/34 |
| 2020/0253320 A1* | 8/2020 | Guard | .................... | G06F 3/011 |

OTHER PUBLICATIONS

Semtech Wireless Charging User Guide TSWITX-G4-EVM Wireless Charging Transmitter.

* cited by examiner

WIRELESS CHARGING ASSEMBLIES FOR SENSORIZED INSOLES, METHODS FOR CHARGING SENSORIZED INSOLES, AND FOOTWEAR SYSTEMS INCLUDING SENSORIZED INSOLES

FIELD

This document relates to sensorized insoles, such as insoles that include pressure and/or temperature sensors. More specifically, this document relates to wireless charging assemblies for sensorized insoles, methods for charging sensorized insoles, and footwear systems including sensorized insoles.

BACKGROUND

U.S. Pat. No. 8,058,837 (Beers et al.) discloses an article of footwear and a footwear housing. The footwear housing includes a charging station that can be used to charge a battery in the footwear housing.

U.S. Patent Application Publication No. 2014/0354218 (Kaynar et al.) discloses a magnetic mounting system configured to charge a personal electronic device with integrated conductive charging of the personal electronic device. The system includes a case configured to connect to the personal electronic device. The case is attached to a printed circuit board, wiring, and a plurality of metal plates. A housing is arranged proximate the casing. The housing includes a plurality of magnets and a plurality of pins. Aligning the plurality of magnets with the plurality of pins detachably couples the case to the housing. Aligning the plurality of pins and the printed circuit board provides electricity from the plurality of pins to the printed circuit board when the case is attached to the housing to charge the personal electronic device in the case.

SUMMARY

The following summary is intended to introduce the reader to various aspects of the detailed description, but not to define or delimit any invention.

Footwear systems are disclosed. According to some aspects, a footwear system includes at least a first sensorized insole. The first sensorized insole has a first insole bulk having a first foot-facing upper surface, at least a first sensor embedded in the first insole bulk for measuring a parameter of a user's first foot, at least a first battery embedded in the first insole bulk for providing energy to the first sensor, and at least a first wireless charging receiver pod embedded in the first insole bulk and spaced from the first foot-facing upper surface for wirelessly receiving energy and providing energy to the first battery. The system further includes a charger for providing energy to the first wireless charging receiver pod. The charger includes a first cable for connecting to an energy source, and at least a first wireless charging transmitter pod electrically connected to the first cable for receiving energy from the first cable and wirelessly transmitting energy to the first wireless charging receiver pod. The first wireless charging transmitter pod is positionable against the first foot-facing upper surface to wirelessly provide energy to the first wireless charging receiver pod through the first insole bulk.

In some examples, the footwear system further includes a second sensorized insole. The second sensorized insole can include a second insole bulk having a second foot-facing upper surface, at least a second sensor embedded in the second insole bulk for measuring a parameter of a user's second foot, at least a second battery embedded in the second insole bulk for providing energy to the second sensor, and at least a second wireless charging receiver pod embedded in the second insole bulk and spaced from the second foot-facing upper surface for wirelessly receiving energy and providing energy to the second battery. The charger can further include at least a second wireless charging transmitter pod that is electrically connected to a second cable for receiving energy from the energy source and for wirelessly transmitting energy to the second wireless charging receiver pod. The second wireless charging transmitter pod can be positionable against the second foot-facing upper surface to wirelessly provide energy to the second wireless charging receiver pod through the second insole bulk.

In some examples, the first wireless charging transmitter pod is further positionable against the second foot-facing upper surface to wirelessly provide energy to the second wireless charging receiver pod through the second insole bulk. The second wireless charging transmitter pod can further be positionable against the first foot-facing upper surface to wirelessly provide energy to the first wireless charging receiver pod through the first insole bulk.

In some examples, the first wireless charging receiver pod includes a first receiver coil, and the first receiver coil is spaced from the first foot-facing upper surface by a first spacing. The second wireless charging receiver pod can include a second receiver coil, and the second receiver coil can be spaced from the second foot-facing upper surface by a second spacing that is different from the first spacing. The first spacing can be, for example, between about 1 mm and about 18 mm, the second spacing can be, for example, between about 1 mm and about 18 mm, and the first spacing and the second spacing can in some examples differ by about 4 mm.

In some examples, the first wireless charging transmitter pod is configured to emit a first electromagnetic field and to dither the first electromagnetic field. The second wireless charging transmitter pod can further be configured to emit a second electromagnetic field and to dither the second electromagnetic field. The first transmitter pod and second transmitter pod can be configured to dither asynchronously.

In some examples, the first wireless charging transmitter pod includes a first transmitter coil and a first set of transmitter magnets arranged around the transmitter coil. The first wireless charging receiver pod can further include a first receiver coil and a first set of receiver magnets arranged around the first receiver coil for magnetically coupling with the first set of transmitter magnets. In some examples, a height of each receiver magnet is less than a height of each transmitter magnet, and a diameter of each receiver magnet is greater than a diameter of each transmitter magnet. In some examples, the first set of transmitter magnets includes a greater number of magnets than the first set of receiver magnets. For example, the first set of transmitter magnets can include between 7 and 15 transmitter magnets spaced around the first transmitter coil, and the first set of receiver magnets can include between 2 and 6 receiver magnets spaced around the first receiver coil. For further example, the first set of transmitter magnets can include 11 transmitter magnets spaced around the first transmitter coil, and the first set of receiver magnets can include 2 receiver magnets positioned on opposite sides of the first receiver coil.

In some examples, the first wireless charging receiver pod includes a first receiver coil that is spaced from the first foot-facing upper surface by a first spacing, and the first wireless charging transmitter pod is configured to detect the first spacing and emit an electromagnetic field of a frequency that is tuned to the first spacing. The first wireless charging transmitter pod can be configured to detect the first spacing by emitting a series of stimulation pulses to the first receiver coil and receiving a series of response pulses back from the first receiver coil. The first spacing can be, for example, between about 1 mm and about 18 mm.

In some examples, the charger comprises the energy source, and the energy source is a battery.

Methods for charging sensorized insoles are also disclosed. According to some aspects, a method for charging one or more sensorized insoles includes: a) with a first sensorized insole received in a first shoe, inserting a first wireless charging transmitter pod through a foot-receiving opening of the first shoe and positioning the first wireless charging transmitter pod against a first foot-facing upper surface of a first insole bulk of the first sensorized insole; and b) transferring energy through the first insole bulk, from the first wireless charging transmitter pod to a first wireless charging receiver pod embedded in the first insole bulk.

In some examples, the method further includes: c) with a second sensorized insole received in a second shoe, inserting a second wireless charging transmitter pod through a foot-receiving opening of the second shoe, and positioning the second wireless charging transmitter pod against a second foot-facing upper surface of a second insole bulk of the second sensorized insole; and d) transferring energy through the second insole bulk of the second sensorized insole, from the second wireless charging transmitter pod to a second wireless charging receiver pod embedded in the second insole bulk.

In some examples, step a) includes magnetically coupling the first wireless charging transmitter pod to the first wireless charging receiver pod, and step c) includes magnetically coupling the second wireless charging transmitter pod to the second wireless charging receiver pod.

In some examples, step b) includes transferring energy from an energy source to the first wireless charging transmitter pod via a first cable, and step d) includes transferring energy from the energy source to the second wireless charging transmitter pod via a second cable.

In some examples, the first wireless charging receiver pod includes a first receiver coil that is spaced from the first foot-facing upper surface by a first spacing, the second wireless charging receiver pod includes a second receiver coil that is spaced from the second foot-facing upper surface by a second spacing that is different from the first spacing, and the method further includes: e) removing the first wireless charging transmitter pod from the first shoe and removing the second wireless charging transmitter pod from the second shoe; f) inserting the second wireless charging transmitter pod through the foot-receiving opening of the first shoe, positioning the second wireless charging transmitter pod against the first foot-facing upper surface, and magnetically coupling the second wireless charging transmitter pod to the first wireless charging receiver pod; and g) transferring energy from the second wireless charging transmitter pod to the first wireless charging receiver pod through the first insole bulk.

In some examples, the first wireless charging receiver pod includes a first receiver coil that is spaced from the first foot-facing upper surface by a first spacing, and step d) includes detecting the first spacing and emitting an electromagnetic field of a frequency that is tuned to the first spacing. Detecting the first spacing can include emitting a series of stimulation pulses from the first transmitter coil to the first receiver coil and receiving a series of response pulses back from the first receiver coil.

In some examples, step b) includes emitting a first electromagnetic field from the first wireless charging transmitter pod and dithering the first electromagnetic field. Step d) can include emitting a second electromagnetic field from the second wireless charging transmitter pod, and dithering the second electromagnetic field asynchronously with the first electromagnetic field.

Wireless charging assemblies for sensorized insoles are also disclosed. According to some aspects, a wireless charging assembly for a sensorized insole includes a wireless charging transmitter pod having a transmitter coil and a set of transmitter magnets arranged around the transmitter coil, and a wireless charging receiver pod having a receiver coil and a set of receiver magnets arranged around the receiver coil for magnetically coupling with the set of transmitter magnets to hold the wireless charging transmitter pod in proximity to the wireless charging receiver pod. A height of each receiver magnet is greater than a height of each transmitter magnet, and a diameter of each receiver magnet is less than a diameter of each transmitter magnet.

In some examples, the set of transmitter magnets includes a greater number of magnets than the set of receiver magnets. For example, the set of transmitter magnets can include between 7 and 15 transmitter magnets spaced around the transmitter coil, and the set of receiver magnets can include between 2 and 6 receiver magnets spaced around the receiver coil. For further example, the set of transmitter magnets can include 11 transmitter magnets spaced around the transmitter coil, and the set of receiver magnets can include 2 receiver magnets positioned on opposite sides of the receiver coil.

Methods for providing a footwear system are also disclosed. According to some aspects, a method for providing a footwear system includes: a) custom manufacturing a sensorized insole for a user by assessing the user's foot and custom fashioning an insole bulk based on the assessment. Custom fashioning the insole includes embedding in the insole bulk at least one sensor, at least one battery for providing energy to the sensor, and at least one wireless charging receiver pod for wirelessly receiving energy and providing the energy to the battery. The insole bulk has a foot-facing upper surface, and the wireless charging receiver pod is embedded in the insole bulk so that a receiver coil of the wireless charging receiver pod is spaced from the foot-facing upper surface by a spacing that is at least partially determined by the assessment. The method further includes b) providing a wireless charging transmitter pod that is configured to wirelessly transmit energy to the wireless charging receiver pod through the insole bulk by positioning the wireless charging transmitter pod against the foot facing upper surface. The wireless charging transmitter pod is configured to detect the spacing and emit an electromagnetic field of a frequency that is tuned to the spacing.

In some examples, the wireless charging transmitter pod is configured to detect the spacing by emitting a series of stimulation pulses to the receiver coil and receiving a series of response pulses back from the receiver coil.

In some examples, the spacing is between about 1 mm and about 18 mm.

In some examples, the wireless charging transmitter pod is configured to first recognize a presence of the receiver coil, and then detect the spacing.

Methods for charging a footwear system are also disclosed. According to some aspects, a method for charging a footwear system includes: a) detecting a spacing between a foot-facing upper surface of an insole bulk and a receiver coil of a wireless charging receiver pod embedded in the insole bulk; and b) providing energy to the wireless charging receiver pod by emitting an electromagnetic field through the insole bulk at a frequency that is tuned to the spacing.

In some examples, step a) includes emitting a series of stimulation pulses from a transmitter coil of a wireless charging transmitter pod to the receiver coil, and receiving a series of response pulses back from the receiver coil. Step b) can include selecting the frequency based on the series of response pulses.

In some examples, the spacing is between about 1 mm and about 18 mm.

In some examples, step a) includes first detecting a presence of the receiver coil, and then detecting the spacing.

Methods for charging one or more sensorized insoles are disclosed. According to some aspects, a method for charging one or more sensorized insoles includes: a) positioning a first wireless charging transmitter pod against a first sensorized insole; and b) transferring energy from the first wireless charging transmitter pod to a first wireless charging receiver pod embedded in the first sensorized insole by emitting a first electromagnetic field from the first wireless charging transmitter pod and dithering the first electromagnetic field.

In some examples, the method further includes: c) positioning a second wireless charging transmitter pod against a second sensorized insole; and d) transferring energy from the second wireless charging transmitter pod to a second wireless charging receiver pod embedded in the second sensorized insole by emitting a second electromagnetic field from the second wireless charging transmitter pod and dithering the second electromagnetic field.

In some examples, step d) includes dithering the second electromagnetic field asynchronously with the first electromagnetic field.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

As used herein, the term 'about' indicates that a referenced value may vary by plus or minus 5%. For example, a reference to a length of 'about 10 mm' indicates that the length may be between 9.5 mm and 10.5 mm.

In this document, unless specified otherwise, all ranges are inclusive of the bounds of the range. For example, the statement that a length may be 'between 5 mm and 15 mm' indicates that the length may be 5 mm, or 15 mm, or any number therebetween.

Generally disclosed herein are wireless charging assemblies for sensorized insoles (such as but not limited to sensory insoles for the prevention of diabetic foot ulcers, such as those sold by Orpyx Medical Technologies Inc. and described in U.S. Pat. No. 10,004,428), and related systems and methods.

The wireless charging assemblies may in some examples be relatively easy to use, particularly for users of limited dexterity and/or mobility. For example, the wireless charging assemblies may be used without necessarily requiring that the sensorized insole(s) be removed from the user's shoe(s), and without necessarily requiring a plug or receptacle of the wireless charging assembly to be mated to a corresponding plug or receptacle of the sensorized insole. That is, in some examples, with the sensorized insole in a shoe, the user may simply drop or place a transmitter pod of the wireless charging assembly into the shoe. The transmitter pod may then magnetically couple to a receiver pod that is embedded in the insole, and commence charging the sensorized insole via an LC (inductor capacitor) circuit.

Furthermore, the wireless charging assemblies may be configured to wirelessly charge sensorized insoles of various thickness, where in use the transmitter pod and receiver pod are not necessarily spaced apart by a pre-set distance. That is, in some instances, the sensorized insoles may be in the form of custom orthotics, which are custom manufactured to fit a user's foot. In such instances, each sensorized insole may have a thickness that is customized to fit the foot of the user. Even for a given user, the sensorized insole for the user's left foot may be of a different thickness than the sensorized insole for the user's right foot. As will be described in further detail below, the wireless charging assemblies may be configured to detect and adjust for the thickness of the insole, in order to effectively charge a given sensorized insole.

Furthermore, the wireless charging assemblies may be configured to have a minimized or reduced peak emission. Particularly, the wireless charging assemblies may include a pair of transmitter pods (i.e. one for each sensorized insole of a pair). The transmitter pods may be configured to transfer energy at an oscillating frequency, to reduce the peak emission of the system. Furthermore, the transmitter pods may be configured to oscillate frequency asynchronously, to even further reduce the peak emission.

Figure 1A:
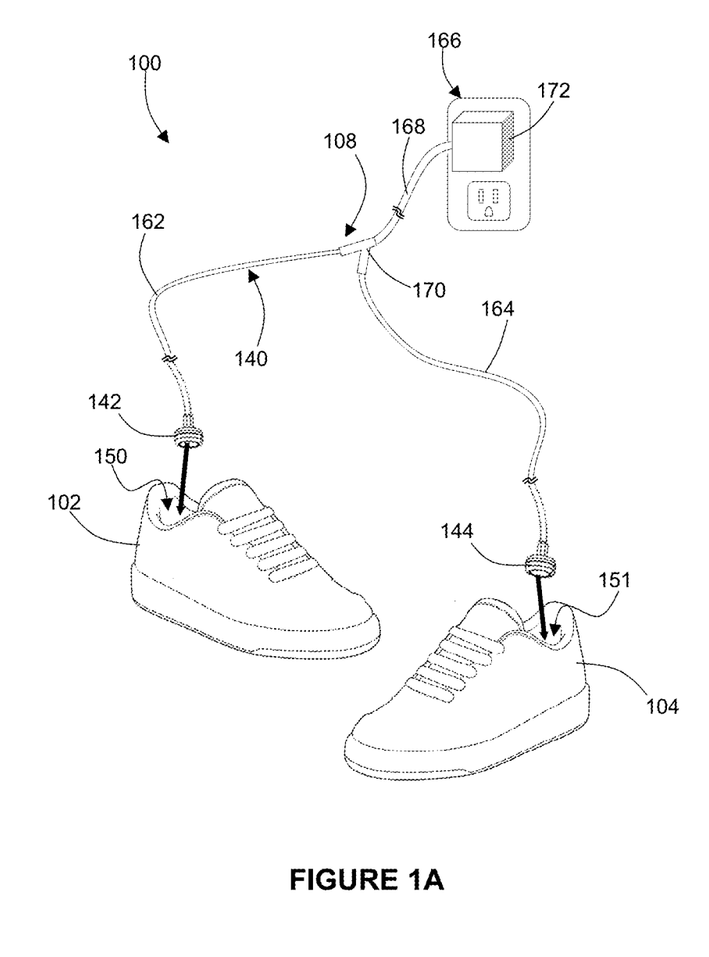
FIG. 1A is a perspective view of an example footwear system, showing a charger in position to be coupled to a pair of sensorized insoles within a pair of shoes.
Figure 1B:
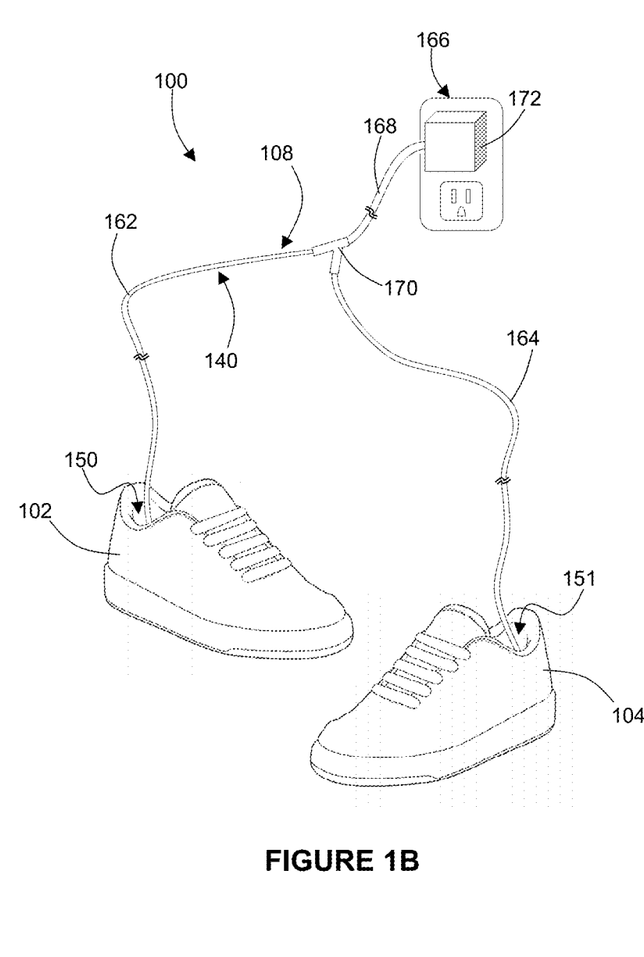
FIG. 1B is a perspective view of the footwear system of FIG. 1A, showing the charger coupled to the insoles.

Referring now to FIGS. 1A and 1B, an example footwear system 100 is shown. The footwear system 100 includes a first shoe 102 and a second shoe 104 (i.e. a left shoe and a right shoe of a pair). A first sensorized insole 106 (shown in FIGS. 2 to 4) is received in the first shoe 102, and a second sensorized insole (not shown) is received in the second shoe 104. When the shoes 102,104 are being worn, the first sensorized insole 106 and second sensorized insole may be used to collect data (e.g. regarding the wearer's health, activity, movement, or gait). When the shoes 102,104 are not being worn, the batteries of the first sensorized insole 106 and the second sensorized insole may be electrically charged by a wireless charging assembly 108, which is described in further detail below.

Figures 2, 3:
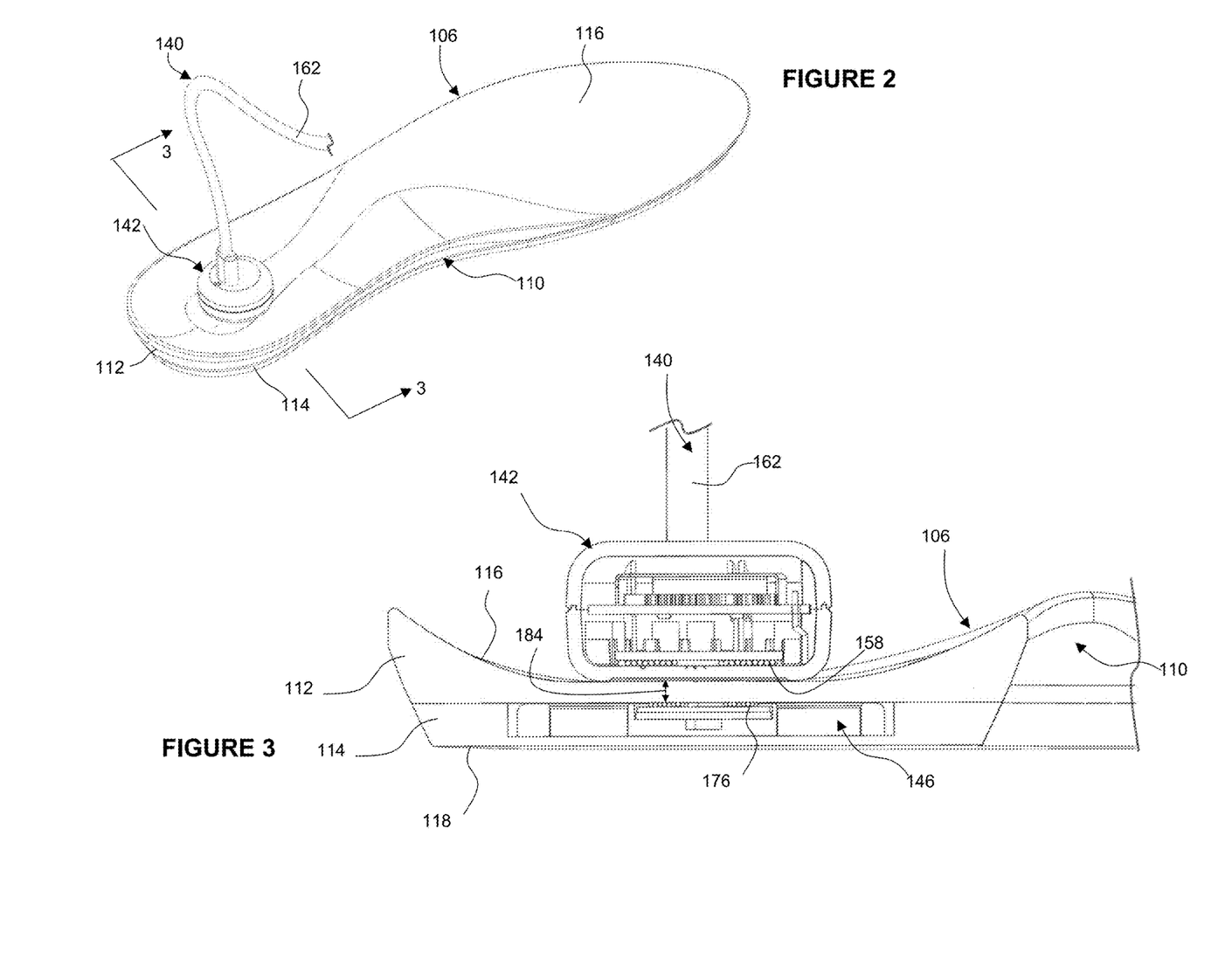
FIG. 2 is a perspective view of a sensorized insole with a transmitter pod of the charger of FIGS. 1A and 1B coupled thereto.
FIG. 3 is a cross section taken along line 3-3 in FIG. 2.

Referring now to FIGS. 2 and 3, the first sensorized insole 106 and a portion of the wireless charging assembly 108 are shown in greater detail. For brevity, only the first sensorized insole 106 and the related features of the wireless charging assembly 108 are shown. The second sensorized insole is similar to the first sensorized insole 106, and is not shown. Furthermore, although the first sensorized insole 106 may be charged while remaining in the first shoe 102 (as shown in FIGS. 1A and 1B), for clarity, the first shoe 102 is not shown in FIGS. 2 and 3.

Referring still to FIGS. 2 and 3, the first sensorized insole 106 includes an insole bulk 110 (also referred to herein as a 'first insole bulk'), which may be made up of one or more layers such as a cushion layer, a support layer, a gel layer, an anti-odor layer, a thermal insulation layer, and/or a foam layer. In the example shown, the first sensorized insole 106 is in the form of an orthotic that is custom manufactured for a user. For example, the user's foot may be assessed (e.g. by a podiatrist, optionally using plaster casting or 3D scanning), and the insole bulk 110 may be custom fashioned based on the assessment, for example in order to support the user's foot, improve foot function, relieve pain, and/or relieve pressure. In the example shown, the insole bulk 110 includes a top layer 112 and a base layer 114. The top layer 112 may in turn include multiple sub-layers, such as an upper finishing layer (not shown), a middle comfort layer (not shown), and a contoured layer (not shown). Likewise, the base layer 114 may include multiple sub-layers. Various sub-layers are described in international patent application no. PCT/CA2020/051520 (publication no. WO 2021/092676), which is incorporated herein by reference in its entirety.

In other examples, the sensorized insoles may be another type of insole, such as a generic insole (e.g. a comfort insole, an athletic insole, a shock-absorbing insole, or a gel insole). Furthermore the sensorized insoles may in some examples be integral with the shoes.

Referring still to FIGS. 2 and 3, the insole bulk 110 has a foot-facing upper surface 116 (also referred to herein as a 'first foot-facing upper surface'), and a ground-facing lower surface 118 (also referred to herein as a 'first ground-facing lower surface'). In use, the foot-facing upper surface 116 faces upwardly towards a user's foot (e.g. contacts the user's skin or sock), and the ground-facing lower surface 118 faces downwardly (e.g. contacts the inner surface of the shoe 102).

Various sensors may be embedded in the insole bulk 110, for measuring a parameter of a user's first foot (e.g. a parameter relating to the user's health, activity, movement, gait, or location). Furthermore, one or more batteries may be embedded in the insole bulk 110, for providing energy to the sensor(s). The sensors may in some examples include one or more of: a heart rate sensor, a blood pressure sensor, an oxygen saturation sensor, an oxygen sensor, a respiratory rate sensor, a blood flow sensor, a cardiac output sensor, a perfusion sensor, a pressure sensor, a temperature sensor, a weight sensor, a body mass index sensor, a moisture sensor, a hydration sensor, a perspiration rate sensor, sweat electrolyte sensor, a bacterial load sensor, an inductance sensor, a resistance sensor, a dielectric sensor, a capacitance sensor, a conductance sensor, an impairment sensor, a sleep sensor, a fatigue sensor, an electrocardiogram sensor, an electromyography sensor, an electroencephalogram sensor, an odor sensor, a taste sensor, a stress sensor, a shear sensor, a respiratory flow rate sensor, a lung function sensor, a GPS, an accelerometer, a gyroscope, a magnetometer, an altimeter, a compass, an image capturing sensor, a limb positioning measurement device, a light sensor, an oxygen sensor, another type of sensor that measures a physiologic(al) characteristic indicative of the functions and activities of a living organism, and combinations thereof.

Figure 4:
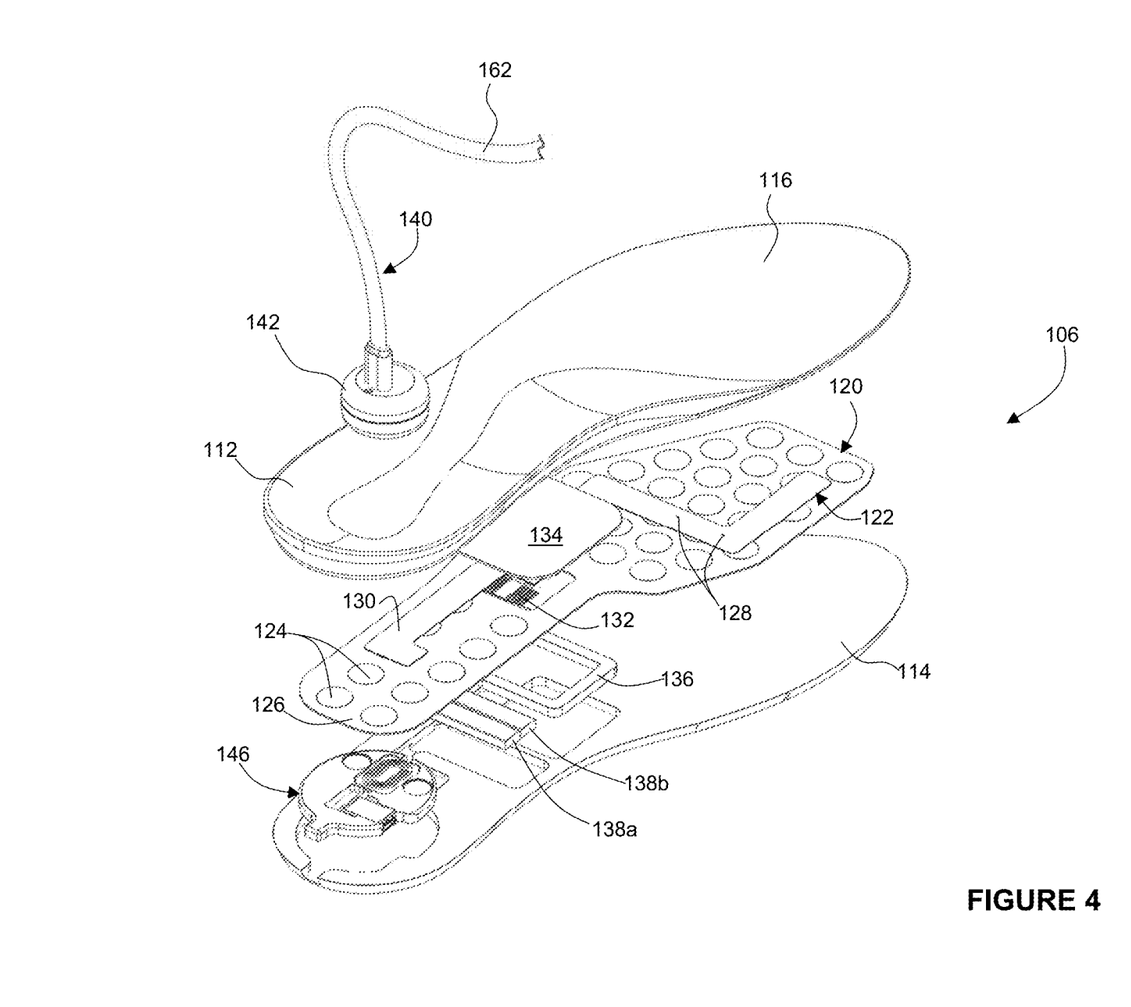
FIG. 4 is an exploded view of the sensorized insole and transmitter pod of FIG. 2.

Referring to FIG. 4, in the example shown, both a pressure sensor array 120 and a temperature sensor array 122 are embedded in the insole bulk 110. The pressure sensor array 120 includes a plurality of pressure sensors 124 (only two of which are labelled) printed on flexible polymer film 126. Likewise, the temperature sensor array 122 includes a plurality of temperature sensors 128 (only two of which are labelled) printed on flexible polymer film 130. Furthermore, a circuit board 132 is embedded in the insole bulk 110, together with a carbon fiber shield 134 and a rigid support 136. The carbon fiber shield 134 serves to distribute pressure to protect the circuit board 132, and the rigid support 136 maintains the carbon fiber shield 134 in position above the circuit board 132. A pair of batteries 138*a*, 138*b* are further embedded in the insole bulk 110, for providing energy to the sensors 124, 128. As will be described below, the batteries 138*a*, 138*b* are chargeable by the wireless charging assembly 108. Such sensor arrays, batteries, and circuit boards are described in international patent application no. PCT/CA2020/051520 (publication no. WO 2021/092676), which is incorporated herein by reference in its entirety.

As used herein, the term 'embedded' indicates that at least a portion of the referenced part is positioned between the layers of the insole bulk 110, or within one or more layers of the insole bulk 110. For example, the referenced part can be nested in a pocket of a first layer, and then covered by a second layer. In the example shown, the pressure sensor array 120, temperature sensor array 122, and circuit board 132 are sandwiched between the top layer 112 and the base layer 114 of the insole bulk 110, while the batteries 138*a*, 138*b* are nested in a pocket of the base layer 114.

As used herein, the term "battery" can refer to any portable and chargeable energy storage device, such as chemical battery (e.g. a lithium ion battery) or a super capacitor.

Similarly to the first sensorized insole 106, the second sensorized insole (not shown) may include a second insole bulk, a second foot-facing upper surface, a second ground-facing lower surface, at least a second sensor embedded in the insole bulk, and at least a second battery embedded in the second insole bulk.

The wireless charging assembly 108 is configured to charge the batteries 138*a*, 138*b* of the first sensorized insole 106 and the batteries of the second sensorized insole. Referring back to FIGS. 1A to 3, in the example shown, the wireless charging assembly 108 includes a charger 140 that in turn includes first 142 and second 144 transmitter pods (also referred to herein as 'wireless charging transmitter pods'). The wireless charging assembly 108 further includes a first receiver pod 146 and a second receiver pod (not shown) (also referred to herein as 'wireless charging receiver pods'), which are embedded in the first insole bulk 110 and the second insole bulk, respectively. The first transmitter pod 142 can wirelessly transmit energy to either of the first receiver pod 146 and the second receiver pod, and the second transmitter pod 144 can wirelessly transmit energy to either of the first receiver pod 146 and the second receiver pod. The first receiver pod 146 wirelessly receives the energy and provides the energy to the batteries 138*a*, 138*b* of the first sensorized insole 106, and the second receiver pod wirelessly receives the energy and provides the energy to the batteries of the second sensorized insole.

More specifically, referring still to FIGS. 2 and 3, the first receiver pod 146 is embedded in the first insole bulk 110, and is spaced from the first foot-facing upper surface 116. In the example shown, the first receiver pod 146 is nested in a pocket of the base layer 114, and is covered by the top layer 112. The first transmitter pod 142 is positionable against the first foot-facing upper surface 116, and wirelessly transmits energy to the first receiver pod 146 through the first insole bulk 110 (i.e. through the top layer 112, in the example shown). Likewise, the second transmitter pod 144 (shown in FIG. 1A) wirelessly transmits energy to the second receiver pod (not shown), and the second receiver pod wirelessly receives the energy and provides the energy to the batteries (not shown) of the second sensorized insole (not shown). Similarly to the first receiver pod 146, the second receiver pod is embedded in the second insole bulk and is spaced from the second foot-facing upper surface, and the second transmitter pod is positionable against the second foot-facing upper surface to wirelessly provide energy to the second wireless charging receiver pod through the second insole bulk.

The first transmitter pod 142 and the first receiver pod 146 are described in greater detail below. For brevity the second transmitter pod 144 and second receiver pod are not shown or described in detail; however, the second transmitter pod 144 is similar to the first transmitter pod 142, and the second receiver pod is similar to the first receiver pod 146.

Figure 5:
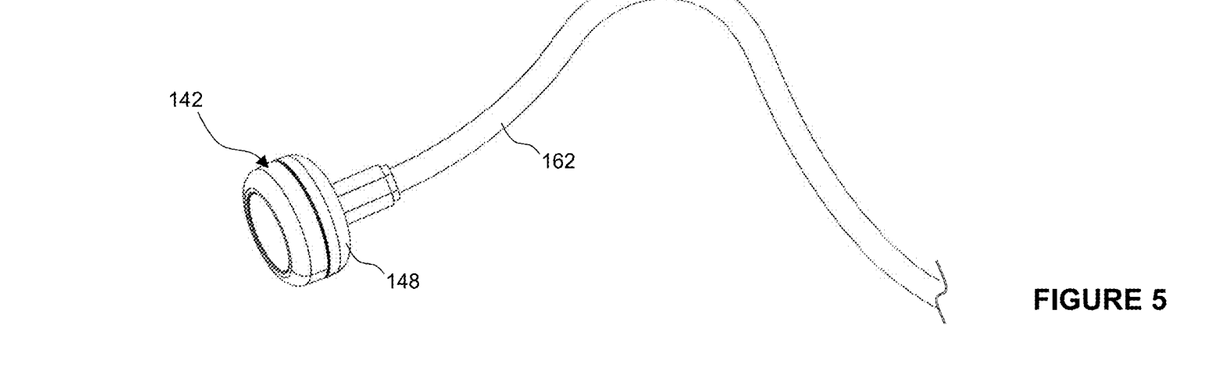
FIG. 5 is an enlarged perspective view of the transmitter pod of FIGS. 2, 3, and 4.
Figure 6:
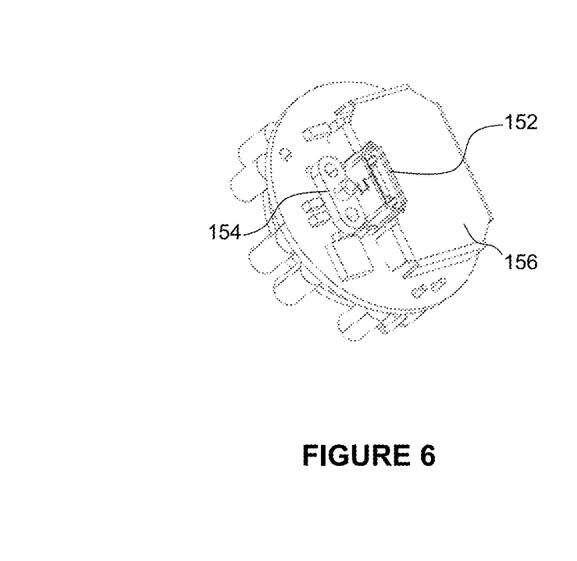
FIG. 6 is a rear perspective view of the transmitter pod of FIG. 5, with a housing thereof removed.
Figure 7:
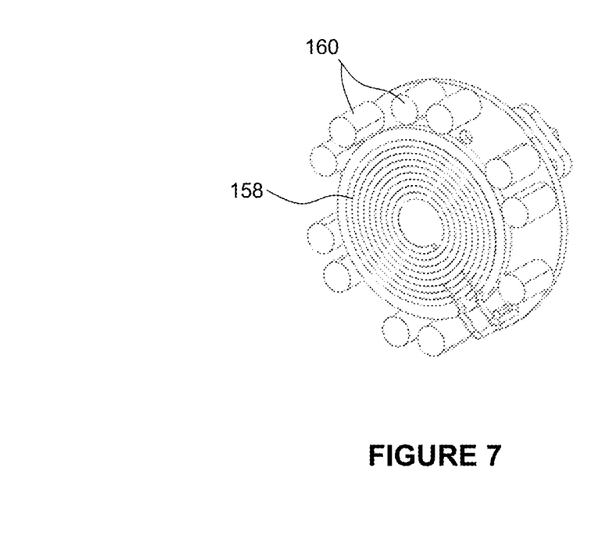
FIG. 7 is a front perspective view of the transmitter pod of FIG. 5, with a housing thereof removed.

Referring now to FIGS. 5 to 7, the first transmitter pod 142 will be described in greater detail. In the example shown, the first transmitter pod 142 includes a housing 148 (shown in FIG. 5). The housing 148 can be sized so that the first transmitter pod 142 can readily pass through a foot-receiving opening 150 of the first shoe 102 or a foot receiving opening 151 of the second shoe 104 (shown in FIGS. 1A and 1B), and so that the first transmitter pod 142 can generally fit within the heel cup (not shown) of the first shoe 102 or second shoe 104 and sit generally flat against the foot-facing upper surface 116. That is, the first transmitter pod 142 may have a relatively small diameter. For example the first transmitter pod 142 may have a diameter of between 20 mm and 40 mm (e.g. about 30 mm) and height of between 10 mm and 20 mm (e.g. about 16 mm).

Referring to FIG. 6, the housing 148 (not shown in FIG. 6) houses a receptacle 152 (also referred to herein as a 'first receptacle') which in the example shown is a micro-USB port, a circuit board (not visible)(also referred to herein as a 'first circuit board'), a light pipe 154 (also referred to herein as a 'first light pipe'), and a shield 156 (also referred to herein as a 'first shield'). Referring to FIG. 7, the housing 148 further houses a transmitter coil 158 (also referred to herein as a 'first transmitter coil'), and a set of transmitter magnets 160 (also referred to herein as a 'first set of transmitter magnets', only two of which are labelled) that are arranged around the transmitter coil 158. The transmitter coil 158 is configured to receive a current from an energy source, and wirelessly induce a current in a receiver coil 176 of the first receiver pod 146 (described below). The transmitter magnets 160 are configured to magnetically couple the first transmitter pod 142 to the first receiver pod 146, to hold the first transmitter pod 142 in proximity to the first receiver pod 146. The first set of transmitter magnets 160 may include, for example, between 7 and 15 transmitter magnets 160. In the example shown, the first set of transmitter magnets 160 includes 11 transmitter magnets 160. The transmitter magnets 160 may be, for example, N38 rare earth magnets. The size of the transmitter magnets 160 may be selected to maximize magnetic coupling to the first receiver pod 146, while minimizing the diameter of the first transmitter pod 142 (i.e. so that the first transmitter pod 142 can readily pass through the foot-receiving opening 150, 151). For example, the transmitter magnets 160 may have a diameter of between about 2 mm and about 8 mm and a height of between about 3 mm and about 10 mm.

The second transmitter pod 144 is configured similarly to the first transmitter pod 142, and includes a second housing (not shown) that is configured so that the second transmitter pod 144 can readily pass through the foot-receiving opening 150 of the first shoe 102 or the foot-receiving opening 151 of the second shoe 104, a second receptacle (not shown), a second circuit board (not shown), a second light pipe (not shown), a second shield (not shown), a second transmitter coil (not shown), and a second set of transmitter magnets arranged around the second transmitter coil (not shown).

Referring back to FIG. 5, in the example shown, the first transmitter pod 142 is electrically connected to a first cable 162 via the receptacle 152 (shown in FIG. 6). Referring back to FIG. 1, the charger 140 further includes a second cable 164, which is electrically connectable to the second transmitter pod 144. The first 162 and second 164 cables are connectable to an energy source (e.g. wall outlet 166), so that the first 142 and second 144 transmitter pods receive energy from the energy source via the first 162 and second 164 cables, respectively. More specifically, in the example shown, the first cable 162 and the second cable 164 are joined to a third cable 168 at a Y-junction 170, and the third cable 168 is electrically connectable to a plug 172 that can plug into the wall outlet 166.

In alternative examples, the energy source can itself be a battery, to allow for portability of the charger.

Figure 8:
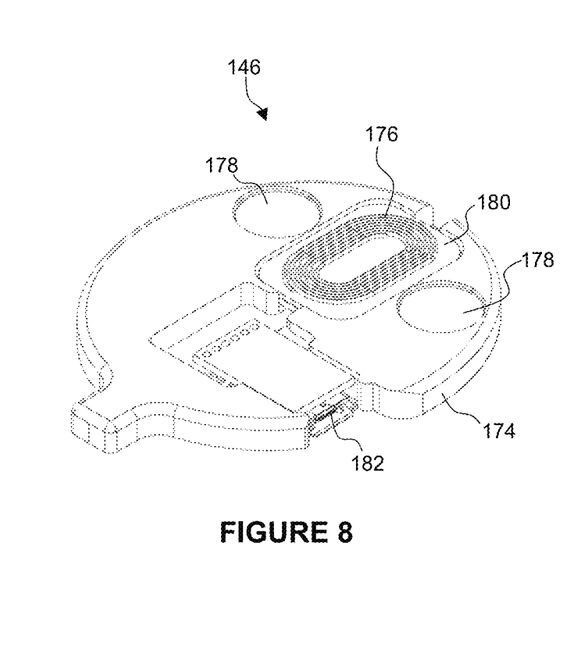
FIG. 8 is a perspective view of a receiver pod of the sensorized insole of FIGS. 2, 3, and 4.
Figure 9:
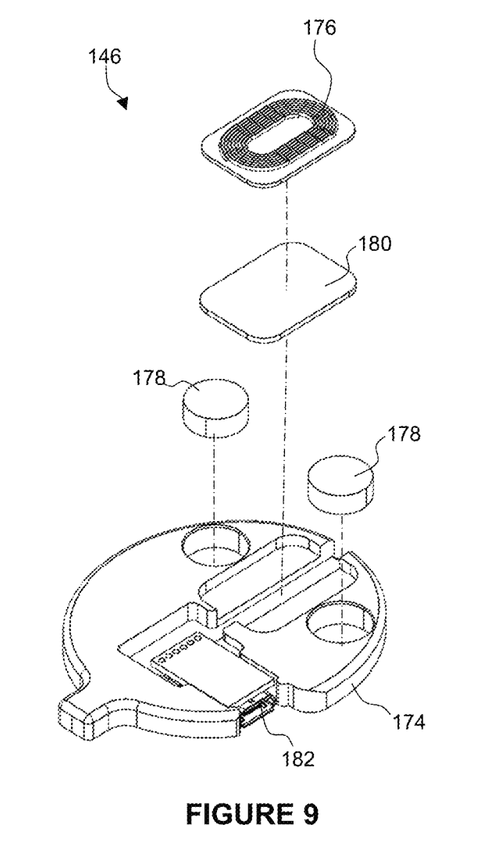
FIG. 9 is an exploded view of the receiver pod of FIG. 8.

Referring now to FIGS. 8 and 9, the first receiver pod 146 will be described in more detail. In the example shown, the first receiver pod 146 includes a housing 174 (also referred to herein as a 'first housing'). The housing 174 is sized so that the first receiver pod 146 can be embedded in the insole bulk 110 without being readily detectable by a user (i.e. without the user feeling an object under their foot). That is, the first receiver pod 146 may have a relatively small thickness. For example the first receiver pod 146 may have a thickness of between about 2 mm and about 5 mm (e.g. about 3.75 mm).

Referring still to FIGS. 8 and 9, the housing 174 supports a receiver coil 176 (also referred to herein as a 'first receiver coil'), and a set of receiver magnets 178 (also referred to herein as a 'first set of receiver magnets'). The receiver coil 176 is configured to wirelessly receive energy by having a current induced therein by the transmitter coil 158. The receiver magnets 178 are configured to magnetically couple to the transmitter magnets 160 (shown in FIGS. 6 and 7), to hold the first receiver pod 146 in proximity to the first transmitter pod 142, so that the transmitter coil 158 can induce a current in the receiver coil 176. The first set of receiver magnets 178 may include, for example, between 2 and 6 receiver magnets 178. In the example shown, the first set of receiver magnets includes 2 receiver magnets 178 positioned on opposite sides of the receiver coil 176. The receiver magnets 178 may be, for example, N52 rare earth magnets. The size of the receiver magnets 178 may be selected to maximize magnetic coupling to the transmitter magnets 160, while minimizing the thickness of receiver pod 146 (i.e. so that the receiver pod 146 is generally not felt under the user's foot). For example, the receiver magnets 178 may have a diameter of between about 3 mm and about 12 mm and a height of between about 2 mm and about 5 mm.

In the example shown, the size constraints of the transmitter pod 142 are different from the size constraints of the receiver pod 146, as the transmitter pod 142 is configured to readily pass through the foot-receiving opening 150 of the first shoe 102 and the foot-receiving opening 151 of the second shoe 104 (and also to fit within the heel cup of the first 102 and second 104 shoes and sit flat against the foot facing upper surface 116), while the receiver pod 146 is configured to be embedded in the insole bulk 110 while remaining generally undetectable. As such, the height of each transmitter magnet 160 is greater than the height of each receiver magnet 178, and the diameter of each transmitter magnet 160 is less than a diameter of each receiver magnet 170. Furthermore, the set of transmitter magnets 160 includes a greater number of magnets than the set of receiver magnets 178. Nevertheless, the set of transmitter magnets 160 can magnetically couple to the set of receiver magnets 178, to hold the receiver pod 146 in proximity to the transmitter pod 142, so that the transmitter coil 158 can induce a current in the receiver coil 176.

In alternative examples, in addition to or as an alternative to the transmitter magnets 160 and receiver magnets 178, other mechanisms may be used to align the transmitter pod 142 to the receiver pod 146 and hold the transmitter pod 142 in proximity to the receiver pod 146. For example, a visual indicator (e.g. in the form of a target) may be provided on the foot-facing upper surface 116, to guide a user in placing the transmitter pod 142 in proximity to the receiver pod 146. For further example, a set of grooves (or another mechanical feature) may be provided for guiding a user in placing the transmitter pod 142 in proximity to the receiver pod 146 and mating the transmitter pod 142 to the insole 106.

Referring still to FIGS. 8 and 9, in the example shown, the receiver pod 146 further includes a carbon fiber shield 180 (also referred to herein as a 'first carbon fiber shield'), which supports the receiver coil 176 and protects the receiver coil 176 from deformation that may occur during use of the sensorized insoles. The receiver pod 146 further includes a receptacle 182 (also referred to herein as a 'first receptacle') in the form of a micro-USB port, which is used to electrically connect the receiver coil 179 to the batteries 138*a*, 138*b* (shown in FIG. 4).

Referring back to FIG. 3, in use of the first sensorized insole 106, when the transmitter pod 142 is positioned against the foot-facing upper surface 116 and magnetically coupled to the receiver pod 146, energy is transferred from the transmitter coil 158 of the transmitter pod 142 to the receiver coil 176 of the receiver pod 146. Particularly, energy is transferred through the insole bulk 110, via an inductor capacitor circuit. In the example shown, the receiver coil 176 is spaced from the foot-facing upper surface 116 by a spacing 184 (also referred to herein as a 'first spacing'), which is defined by the thickness of the portion of the top layer 112 that overlies the receiver coil 176. Likewise, in the second sensorized insole (not shown), the second receiver coil is spaced from the second foot-facing upper surface by a second spacing. As noted above, in the example shown, the first sensorized insole 106 and the second sensorized insole (not shown) are in the form of custom orthotics, which are custom manufactured to fit a user's feet. Accordingly, the size of first spacing 184 may be unique to each user, as the thickness of the top layer 112 of the first sensorized insole 106 is determined at least in part by the assessment of the user's foot. Likewise, the size of the second spacing (not shown) may be unique to each user, as the thickness of the top layer of the second sensorized insole is determined at least in part by the assessment of the user's foot. For example, for a user with high arches, the top layer 112 may be relatively thick and the spacing 184 may thus be relatively large. On the contrary, for a user with relatively low arches, the top layer 112 may be relatively thin and the spacing 184 may thus be relatively small. Furthermore, even for a given user, the first spacing 184 may be different from the second spacing (e.g. in the case where a user's left foot has a different arch height from the user's right foot). More specifically, the first spacing 184 and the second spacing may on average be about 6 mm, but may vary between about 1 mm (e.g. where the top layer 112 includes only an upper finishing layer and the middle comfort layer and contour layer are omitted) and up to 18 mm. Accordingly, the first spacing 184 may differ between users by up to 17 mm, or more commonly, by up to about 4 mm. Furthermore, the first spacing 184 and the second spacing may differ between feet by up to 17 mm, or more commonly, by up to about 4 mm.

In order to account for the variable nature of the first spacing 184 and the second spacing, the first transmitter pod 142 is configured to detect the spacing of the insole to which it is coupled, and adjust its output accordingly, in order to effectively transfer energy at a given spacing. Likewise, the second transmitter pod 144 is configured to detect the spacing of the insole to which it is coupled, and adjust its output accordingly, in order to effectively transfer energy at a given spacing. That is, when coupled to the first sensorized insole 106, the first transmitter pod 142 will detect the first spacing 184, and emit an electromagnetic field of a frequency that is tuned to the first spacing 184. In order to do this, the first transmitter pod 142 is configured to emit a series of stimulation pulses to the receiver coil 176, receive a series of response pulses back from the receiver coil 176, and adjust the output thereof based on the response pulses. More specifically, the transmitter coil 158 is configured to send out a series of stimulation pulses (also referred to as 'pings') of a narrow band that is close to the resonant frequency of the circuit. When these stimulation pulses are received by the receiver coil 176, response pulses are emitted, and the response pulses are detected by the transmitter coil 158. When the response pulses are detected, the transmitter pod 142 recognizes the presence of the receiver coil 176 in proximity to the transmitter coil 158, and begins to emit pings at a broader band. The receiver coil 176 will continue to emit response pulses, and based on the response pulses, the transmitter pod 142 will determine an operating frequency (i.e. a highest efficiency frequency). The transmitter pod 142 will then select that frequency and begin transferring energy at that frequency. For example, if the transmitter coil 158 has a diameter of about 18 mm, and the transmitter coil 158 and receiver coil 176 are spaced apart by between about 1 mm and 18 mm, the operating frequency may be between about 0.43 MHz and 0.45 MHz. The second transmitter pod 144 operates in a similar fashion.

Because the transmitter pods 142, 144 are configured to adjust their output based on the spacing of the sensorized insole to which they are coupled, the transmitter pods 142, 144 can be manufactured in bulk, even though the sensorized insoles themselves may be custom manufactured for each user. Furthermore, because the transmitter pods 142, 144 are configured to adjust their output based on the spacing of the sensorized insole to which they are coupled, the user need not necessarily have a transmitter pod that is designated for a left sensorized insole and a transmitter pod that is designated for a right sensorized insole. Rather, the first transmitter pod 142 and second transmitter pod 144 can be interchangeable. That is, the first transmitter pod 142 can be positioned against either the foot-facing upper surface 116 of the first sensorized insole 106 to wirelessly provide energy to the first receiver pod 146 through the first insole bulk 110, or against the foot-facing upper surface of the second sensorized insole to wirelessly provide energy to the second wireless charging receiver pod through the second insole bulk. Likewise, the second transmitter pod 144 can be positioned against either the second foot-facing upper surface to wirelessly provide energy to the second wireless charging receiver pod through the second insole bulk, or against the first foot-facing upper surface 116 to wirelessly provide energy to the first wireless charging receiver pod through the first insole bulk 110.

In addition, in order to minimize or reduce conducted emissions from the wireless charging assembly 108, the electromagnetic field emitted from the first transmitter pod 142 (also referred to herein as a 'first electromagnetic field') may be dithered, and the electromagnetic field emitted from the second transmitter pod 144 (also referred to herein as a 'second electromagnetic field') may be dithered. That is, energy may be transferred at a frequency that oscillates slightly around the operating frequency, to reduce the peak emission of the system. Furthermore, the second electromagnetic field may be dithered asynchronously with the first electromagnetic field, to even further reduce peak emissions.

In order to mitigate any issues caused by the generation of heat during charging, the first transmitter pod 142 may be configured to detect the temperature in the vicinity of the transmitter coil 158, and turn off for a preset time period (e.g. about 20 seconds) if the temperature exceeds a predetermined threshold (e.g. a temperature of about 50 degrees Celsius). The second transmitter pod 144 may be similarly configured.

In general, in use, the first sensorized insole 106 and the second sensorized insole can be positioned in a user's shoes 102, 104, and the shoes 102, 104 can be worn. When the shoes 102 104 are removed from the user's feet, the first sensorized insole 106 and second sensorized insole can be charged. As noted above, the user need not necessarily remove the first sensorized insole 106 and second sensorized insole from the shoes 102, 104; the first sensorized insole 106 and second sensorized insole can remain in the shoes 102, 104 during charging. That is, with the first sensorized insole 106 remaining in the first shoe 102 and the second sensorized insole remaining in the second shoe 104, the user can insert the first transmitter pod 142 through the foot-receiving opening 150 of the first shoe 102 and position the first transmitter pod 142 against the first foot-facing upper surface 116 of the first insole bulk 110, and insert the second transmitter pod 144 through the foot-receiving opening 151 of the second shoe 104 and position the second transmitter pod 144 against the second foot-facing upper surface of the second insole bulk. This can be achieved, for example, by simply dropping the first transmitter pod 142 into the first shoe 102 and allowing the first transmitter pod 142 to magnetically couple to the first receiver pod 146, and dropping the second transmitter pod 144 into the second shoe 104 and allowing the second transmitter pod 144 to magnetically couple to the second receiver pod. As noted above, the transmitter pods 142, 144 are each configured to charge the first sensorized insole 106 and the second sensorized insole, even if the first sensorized insole 106 and the second sensorized insole have different thicknesses. Accordingly, the user can drop either transmitter pod 142, 144 into either shoe 102, 104 (i.e. the transmitter pods 142, 144 could be removed from the shoes 102, 104 and swapped, so that the second transmitter pod 144 is inserted through the foot-receiving opening 150 of the first shoe 102, positioned against the foot-facing upper surface 116 of the first insole bulk 110, and magnetically coupled to the first receiver pod 146). Energy will then be transferred from the energy source (i.e. the wall outlet 166) to the first 142 and second 144 transmitter pods via the cables 162, 164, 168, and from the first 142 and second 144 transmitter pods to the first 146 and second receiver pods, respectively.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A footwear system comprising
at least a first sensorized insole having a first insole bulk having a first foot-facing upper surface, at least a first sensor embedded in the first insole bulk for measuring a parameter of a user's first foot, at least a first battery embedded in the first insole bulk for providing energy to the first sensor, and at least a first wireless charging receiver pod embedded in the first insole bulk and spaced from the first foot-facing upper surface for wirelessly receiving energy and providing energy to the first battery;
a second sensorized insole having a second insole bulk having a second foot-facing upper surface, at least a second sensor embedded in the second insole bulk for measuring a parameter of the user's second foot, at least a second battery embedded in the second insole bulk for providing energy to the second sensor, and at least a second wireless charging receiver pod embedded in the second insole bulk and spaced from the second foot-facing upper surface for wirelessly receiving energy and providing energy to the second battery;
a charger for providing energy to the first wireless charging receiver pod and the second wireless charging receiver pod, the charger comprising a first cable for connecting to an energy source, at least a first wireless charging transmitter pod electrically connected to the first cable for receiving energy from the first cable and wirelessly transmitting energy to the first wireless charging receiver pod and the second wireless charging receiver pod, and at least a second wireless charging transmitter pod electrically connected to a second cable for receiving energy from the energy source and for wirelessly transmitting energy to the second wireless charging receiver pod and the first wireless charging receiver pod;

wherein the first wireless charging transmitter pod is positionable against the first foot-facing upper surface to wirelessly provide energy to the first wireless charging receiver pod through the first insole bulk and against the second foot-facing upper surface to wirelessly provide energy to the second wireless charging receiver pod through the second insole bulk;

wherein the second wireless charging transmitter pod is positionable against the second foot-facing upper surface to wirelessly provide energy to the second wireless charging receiver pod through the second insole bulk and against the first foot-facing upper surface to wirelessly provide energy to the first wireless charging receiver pod through the first insole bulk;

wherein the first wireless charging receiver pod comprises a first receiver coil that is spaced from the first foot-facing upper surface by a first spacing, and the second wireless charging receiver pod comprises a second receiver coil that is spaced from the second foot-facing upper surface by a second spacing that is different from the first spacing; and wherein the first wireless charging transmitter pod and the second wireless charging transmitter pod are each configured to detect the first spacing by emitting a series of stimulation pulses to the first receiver coil and receiving a series of response pulses back from the first receiver coil and to detect the second spacing by emitting the series of stimulation pulses to the second receiver coil and receiving a second series of response pulses back from the second receiver coil.

2. The footwear system of claim 1, wherein
the first wireless charging transmitter pod is configured to emit a first electromagnetic field and to dither the first electromagnetic field;
the second wireless charging transmitter pod is configured to emit a second electromagnetic field and to dither the second electromagnetic field; and
the first transmitter pod and second transmitter pod are configured to dither asynchronously.

3. The footwear system of claim 1, wherein:
the first wireless charging transmitter pod comprises a first transmitter coil and a first set of transmitter magnets arranged around the transmitter coil; and
the first wireless charging receiver pod comprises a first set of receiver magnets arranged around the first receiver coil for magnetically coupling with the first set of transmitter magnets.

4. The footwear system of claim 3, wherein a height of each receiver magnet is less than a height of each transmitter magnet, and a diameter of each receiver magnet is greater than a diameter of each transmitter magnet.

5. The footwear system of claim 3 wherein the first set of transmitter magnets comprises a greater number of magnets than the first set of receiver magnets.

6. The footwear system of claim 3, wherein:
the first set of transmitter magnets comprises between 7 and 15 transmitter magnets spaced around the first transmitter coil; and
the first set of receiver magnets comprises between 2 and 6 receiver magnets spaced around the first receiver coil.

7. The footwear system of claim 1 wherein:
the first wireless charging transmitter pod is configured to emit an electromagnetic field of a frequency that is tuned to the first spacing.

8. The footwear system of claim 1, wherein the first spacing is between about 1 mm and about 18 mm.

9. A method for charging a pair of sensorized insoles, comprising:
a. with a first sensorized insole received in a first shoe, inserting a first wireless charging transmitter pod through a foot-receiving opening of the first shoe and positioning the first wireless charging transmitter pod against a first foot-facing upper surface of a first insole bulk of the first sensorized insole;
b. transferring energy through the first insole bulk, from the first wireless charging transmitter pod to a first wireless charging receiver pod embedded in the first insole bulk, wherein the first wireless charging receiver pod comprises a first receiver coil that is spaced from the first foot-facing upper surface by a first spacing;
c. between steps a. and b., detecting the first spacing by emitting a series of stimulation pulses from the first transmitter pod to the first receiver coil and receiving a series of response pulses back from the first receiver coil;
d. with a second sensorized insole received in a second shoe, inserting a second wireless charging transmitter pod through a foot-receiving opening of the second shoe, and positioning the second wireless charging transmitter pod against a second foot-facing upper surface of a second insole bulk of the second sensorized insole; and
e. transferring energy through the second insole bulk of the second sensorized insole, from the second wireless charging transmitter pod to a second wireless charging receiver pod embedded in the second insole bulk, wherein the second wireless charging receiver pod comprises a second receiver coil that is spaced from the second foot-facing upper surface by a second spacing that is different from the first spacing;
f. removing the first wireless charging transmitter pod from the first shoe and removing the second wireless charging transmitter pod from the second shoe;
g. inserting the second wireless charging transmitter pod through the foot-receiving opening of the first shoe, positioning the second wireless charging transmitter pod against the first foot-facing upper surface; and
h. transferring energy from the second wireless charging transmitter pod to the first wireless charging receiver pod through the first insole bulk.

10. The method of claim 9, wherein step a. comprises magnetically coupling the first wireless charging transmitter pod to the first wireless charging receiver pod, and step d. comprises magnetically coupling the second wireless charging transmitter pod to the second wireless charging receiver pod.

11. The method of claim 9, wherein step b. comprises transferring energy from an energy source to the first wireless charging transmitter pod via a first cable, and step e. comprises transferring energy from the energy source to the second wireless charging transmitter pod via a second cable.

12. The method of claim 9,
wherein step g. comprises magnetically coupling the second wireless charging transmitter pod to the first wireless charging receiver pod.

13. The method of claim 9, wherein step b. comprises emitting an electromagnetic field of a frequency that is tuned to the first spacing.

14. The method of claim 9, wherein step b. comprises emitting a first electromagnetic field from the first wireless charging transmitter pod and dithering the first electromagnetic field, and wherein step e. comprises emitting a second electromagnetic field from the second wireless charging transmitter pod, and dithering the second electromagnetic field asynchronously with the first electromagnetic field.

15. The footwear system of claim 1, wherein the first wireless charging transmitter pod is configured to send out a series of narrow band stimulation pulses and detect a first series of response pulses from the first receiver coil to recognize the presence of the first receiver coil, then emit a series of broad band stimulation pulses and detect a second series of response pulses from the first receiver coil.

16. The footwear system of claim 15, wherein the first wireless charging transmitter pod is configured to determine an operating frequency based on the second series of response pulses, and wirelessly transmit energy at the operating frequency.

* * * * *